US008788021B1

(12) United States Patent
Flusberg et al.

(10) Patent No.: US 8,788,021 B1
(45) Date of Patent: *Jul. 22, 2014

(54) LIVE BEING OPTICAL ANALYSIS SYSTEM AND APPROACH

(75) Inventors: Benjamin A. Flusberg, Stanford, CA (US); Eric David Cocker, Menlo Park, CA (US); Juergen Claus Jung, Palo Alto, CA (US); Mark Jacob Schnitzer, Palo Alto, CA (US)

(73) Assignee: The Board of Trustees of the Leland Stanford Junior Univerity, Palo Alto, CA (US)

( * ) Notice: Subject to any disclaimer, the term of this patent is extended or adjusted under 35 U.S.C. 154(b) by 913 days.

This patent is subject to a terminal disclaimer.

(21) Appl. No.: 11/338,598

(22) Filed: Jan. 24, 2006

Related U.S. Application Data

(60) Provisional application No. 60/646,858, filed on Jan. 24, 2005, provisional application No. 60/646,711, filed on Jan. 24, 2005.

(51) Int. Cl.
*A61B 6/08* (2006.01)
*A61B 5/00* (2006.01)
*G01J 3/44* (2006.01)
*G02B 6/06* (2006.01)

(52) U.S. Cl.
CPC .............. *A61B 5/0059* (2013.01); *A61B 5/0068* (2013.01); *A61B 5/0071* (2013.01); *A61B 5/0075* (2013.01); *A61B 5/4064* (2013.01); *A61B 5/6814* (2013.01); *A61B 5/0013* (2013.01); *A61B 5/0062* (2013.01); *G01J 3/44* (2013.01); *G01J 3/4406* (2013.01)

USPC ............ 600/473; 600/476; 356/318; 385/117

(58) Field of Classification Search
USPC .................................................. 600/476, 473
See application file for complete search history.

(56) References Cited

U.S. PATENT DOCUMENTS

| | | |
|---|---|---|
| 5,201,318 A | 4/1993 | Rava et al. |
| 5,345,941 A | 9/1994 | Rava et al. |
| 5,419,323 A | 5/1995 | Kittrell et al. |
| 5,421,337 A | 6/1995 | Richards-Kortum |
| 5,421,339 A | 6/1995 | Ramanujam et al. |
| 5,562,100 A | 10/1996 | Kittrell et al. |
| 5,612,540 A | 3/1997 | Richards-Kortum |
| 5,623,932 A | 4/1997 | Ramanujam et al. |

(Continued)

OTHER PUBLICATIONS

JC Jung, AD Mehta, E Aksay, R Stepnoski, and MJ Schnitzer. "In Vivo Mammalian Brain Imaging Using One- and Two-Photon Fluorescence Microendoscopy", J Neurophysiology 92:3121-3133, May 2004.*

(Continued)

*Primary Examiner* — Long V. Le
*Assistant Examiner* — Angela M Hoffa
(74) *Attorney, Agent, or Firm* — Crawford Maunu PLLC (57) ABSTRACT

Analysis of live beings is facilitated. According to an example embodiment of the present invention, a light-directing arrangement such as an endoscope is mounted to a live being. Optics in the light-directing arrangement are implemented to pass source light (e.g., laser excitation light) into the live being, and to pass light from the live being for detection thereof. The light from the live being may include, for example, photons emitted in response to the laser excitation light (i.e., fluoresced). The detected light is then used to detect a characteristic of the live being.

33 Claims, 6 Drawing Sheets

(56) References Cited

U.S. PATENT DOCUMENTS

| | | | |
|---|---|---|---|
| 5,697,373 | A | 12/1997 | Richards-Kortum |
| 5,699,795 | A | 12/1997 | Richards-Kortum |
| 5,791,345 | A | 8/1998 | Ishihara et al. |
| 5,842,995 | A | 12/1998 | Mahadevan-Jansen |
| 5,916,171 | A * | 6/1999 | Mayevsky ................... 600/476 |
| 5,920,399 | A | 7/1999 | Sandison et al. |
| 5,929,985 | A | 7/1999 | Sandison et al. |
| 5,954,053 | A * | 9/1999 | Chance et al. ............... 600/310 |
| 5,991,653 | A | 11/1999 | Richards-Kortum |
| 6,007,208 | A | 12/1999 | Dickensheets et al. |
| 6,095,982 | A | 8/2000 | Richards-Kortum |
| 6,122,536 | A * | 9/2000 | Sun et al. .................... 600/341 |
| 6,135,965 | A | 10/2000 | Tumer et al. |
| 6,187,289 | B1 | 2/2001 | Richards-Kortum |
| 6,241,662 | B1 | 6/2001 | Richards-Kortum |
| 6,258,576 | B1 | 7/2001 | Richards-Kortum |
| 6,370,422 | B1 | 4/2002 | Richards-Kortum |
| 6,423,956 | B1 | 7/2002 | Mandella et al. |
| 6,485,413 | B1 | 11/2002 | Boppart et al. |
| 6,571,118 | B1 | 5/2003 | Utzinger et al. |
| 6,580,941 | B2 | 6/2003 | Webb |
| 6,593,101 | B2 | 7/2003 | Richards-Kortum |
| 6,639,674 | B2 | 10/2003 | Sokolov et al. |
| 6,697,666 | B1 | 2/2004 | Richards-Kortum |
| 6,766,184 | B2 | 7/2004 | Utzinger et al. |
| 6,815,186 | B2 * | 11/2004 | Clark, Jr. .................... 435/183 |
| 7,023,558 | B2 * | 4/2006 | Fee et al. .................... 356/479 |
| 7,091,500 | B2 | 8/2006 | Schnitzer ................. 250/458.1 |
| 7,307,774 | B1 * | 12/2007 | Schnitzer et al. ............. 359/290 |
| 7,336,988 | B2 * | 2/2008 | Schnitzer .................... 600/476 |
| 7,384,396 | B2 * | 6/2008 | Samuels et al. .............. 600/309 |
| 8,068,899 | B2 * | 11/2011 | Llewellyn et al. ............ 600/478 |
| 8,346,346 | B1 * | 1/2013 | Schnitzer et al. ............. 600/476 |
| 2002/0065468 | A1 | 5/2002 | Utzinger et al. |
| 2002/0080359 | A1 | 6/2002 | Denk et al. |
| 2002/0110590 | A1 | 8/2002 | Shaked et al. |
| 2002/0127632 | A1 | 9/2002 | Richards-Kortum |
| 2002/0135752 | A1 | 9/2002 | Sokolov et al. |
| 2002/0140942 | A1 * | 10/2002 | Fee et al. ..................... 356/477 |
| 2002/0141714 | A1 | 10/2002 | Reed et al. |
| 2002/0146202 | A1 | 10/2002 | Reed et al. |
| 2003/0031410 | A1 | 2/2003 | Schnitzer |
| 2003/0103262 | A1 | 6/2003 | Descour et al. |
| 2003/0117715 | A1 | 6/2003 | Schnitzer |
| 2003/0118305 | A1 | 6/2003 | Reed et al. |
| 2003/0142934 | A1 * | 7/2003 | Pan et al. .................... 385/116 |
| 2004/0023415 | A1 | 2/2004 | Sokolov et al. |
| 2004/0064053 | A1 | 4/2004 | Chang et al. |
| 2004/0143190 | A1 | 7/2004 | Schnitzer |
| 2004/0162489 | A1 | 8/2004 | Richards-Kortum |
| 2004/0260148 | A1 | 12/2004 | Schnitzer |
| 2005/0080343 | A1 | 4/2005 | Richards-Kortum |
| 2005/0148818 | A1 * | 7/2005 | Mesallum ................... 600/116 |
| 2005/0157981 | A1 | 7/2005 | Berier et al. |
| 2005/0207668 | A1 | 9/2005 | Perchant et al. |
| 2005/0242298 | A1 | 11/2005 | Genet et al. |
| 2012/0281218 | A1 * | 11/2012 | Schnitzer et al. ............. 356/432 |

OTHER PUBLICATIONS

Protein Localization by Fluorescence Microscopy: A Practical Approach by Victoria Allen, Published by Oxford University Press, 2000, p. 118.*

Gobel et al, "Miniaturized two-photon microscope based on a flexible boherent bundle and a gradient-index lens objective", Optics Letters, vol. 29, No. 21, Nov. 1, 2004, pp. 2521-2523.*

Thomas D. Wang et al. "Confocal fluorescence microscope with dual-axis architecture and biaxial postobjective scanning." Jul./Aug. 2004. *Journal of biomedical Optics.* vol. 9 No. 4:735-742.

Fossum E. Digital camera system-on-a-chip. IEEE Micro 1998;18(3):8-15.

Theuwissen A. CMOS image sensors: state-of-the-art. Solid-State Electronics 2008;52(1):1401-6.

Helmchen F, Fee M, Tank D, Denk W. A miniature head-mounted two-photon microscope: high resolution brain imaging in freely moving animals. Neuron 2001;31(1):903-12.

* cited by examiner

LIVE BEING OPTICAL ANALYSIS SYSTEM AND APPROACH

RELATED PATENT DOCUMENTS

This patent document claims the benefit, under 35 U.S.C. §119(e), of U.S. Provisional Patent Application No. 60/646,711, entitled "Live Being Optical Analysis System and Approach" and filed on Jan. 24, 2005; this patent document further claims the benefit, under 35 U.S.C. §119(e), of U.S. Provisional Patent Application No. 60/646,858, entitled "Optical Analysis Systems and Approaches" and also filed on Jan. 24, 2005.

FEDERALLY-SPONSORED RESEARCH AND DEVELOPMENT

This invention was made with Government Support under contract 0352456 awarded by the National Science Foundation and contract N00014-04-1-0826 awarded by the Department of the Navy. The U.S. Government has certain rights in this invention.

FIELD OF THE INVENTION

The present invention relates generally to optical analysis, and more particularly to in vivo imaging approaches involving the analysis of live beings.

BACKGROUND

A variety of approaches to optical imaging have been used for many different applications, such as for research, testing and treatment of diseases or other illnesses. For example, endoscopes and other imaging devices have been used for imaging tissue in anesthetized animals.

With the growing number of approaches to the analysis of live beings, there has been growth in technologies benefiting from such analysis as well as in the need to perform extensive analysis of the impact of such technologies. For example, imaging cellular and sub-cellular functions in live animals is desirable for many areas of biological research. Fluorescent probes have been implemented for expression in specific cell classes of genetically-engineered animals. Fluorescence microendoscopy involving one- or two-photon fluorescence excitation has been used to image biological cells in tissue, and have been implemented with relatively deep-tissue analysis. See, e.g., J. C. Jung and M. J. Schnitzer, Opt. Lett. 28, 902 (2003); see also J. C. Jung, A. D. Mehta, E. Aksay, R. Stepnoski, and M. J. Schnitzer, J. Neurophysiol. 92, 3121 (2004). These and other approaches are useful, for example, in the development of new drugs and therapeutics.

In many applications, optical imaging requires anesthetized or otherwise immobilized subjects. These requirements have presented challenges not only to the ability to obtain optical data, but to the analysis of subjects. For instance, an anesthetized or immobile state may be available under limited conditions of time and environment.

The above and other issues have presented challenges to optical analysis approaches and, in particular, to optical imaging in live beings.

SUMMARY

The present invention is directed to overcoming the above-mentioned challenges and others related to the types of devices and applications discussed above and in other applications. These and other aspects of the present invention are exemplified in a number of illustrated implementations and applications, some of which are shown in the figures and characterized in the claims section that follows.

According to an example embodiment, an optical analysis approach involves connecting a light-directing arrangement to a live being for stimulating and detecting a response from the live being. A light source, such as a laser, provides light to the light-directing arrangement, which couples the light into a portion of the live being using a directing mechanism such as a micro-mirror or micro-movable actuator. The light is impinged upon a target region of the live being. An optical response from the live being is collected and passed to a light detector for analysis. The connected nature of the light-directing arrangement facilitates the maintenance of a spatial relationship between the directing mechanism with the live being. With this approach, a live being can be analyzed using a fixed light-directing arrangement without necessarily anesthetizing the being and, where appropriate, facilitating the ability of the live being to move while under analysis.

According to another example embodiment of the present invention, a freely-moving live being is analyzed. A housing is fixed to the live being and a light scanning arrangement is coupled to the housing to hold the light scanning arrangement in a position relative to the live being. Stimulation light is passed to the light scanning arrangement and, using the light scanning arrangement, the stimulation light is selectively scanned across a target portion of the live being while the freely-moving being moves about a controlled environment. Response light is passed from the light director arrangement to a light detector, which receives and detects the response light. The detector further generates a signal corresponding to the detected light for use in analyzing the live being.

In another example embodiment of the present invention, brain tissue in a freely-moving live animal is imaged using an in vivo fluorescence approach. An endoscope arrangement is fastened to the skull of the freely-moving live animal using, for example, screws or other fasteners. The endoscope arrangement is thus held in a position relative to the live animal's brain tissue, such that the animal can move freely over a period of time. In this context, free movement of the animal involves, for example, movement of the animal within a cage or to the extent that light and/or electrical conduits coupled to the endoscope arrangement allow. Pulsed laser stimulation light is passed to the live animal's brain tissue via the endoscope arrangement. The wavelength of the pulsed laser stimulation is selected to stimulate a fluorescent response that is limited to a point of focus of the pulsed laser stimulation light in the brain tissue. A point of focus, in this context, involves a small area, such as that immediately adjacent a focal point in a plane of focus of the laser light. Photons emitted via the fluorescent response of the brain tissue over the period of time are passed via the endoscope to a detector where the photons are detected. These detected photons are then analyzed to detect a condition of the live animal.

According to another example embodiment of the present invention, an optical analysis system facilitates in vivo analysis of a freely-moving live being. The system includes a light source, a light scanning arrangement and a housing to which the light scanning arrangement is coupled. A light stimulation conduit such as a fiber optic cable passes stimulation light from the light source to the light scanning arrangement. The housing is fastened to the freely-moving live being (e.g., to its skull where brain tissue is to be imaged) and, thereby, holds the light scanning arrangement in a position relative to the live being while it moves about a controlled environment such as in a cage. The light scanning arrangement selectively scans stimulation light from the light source across a target portion of the live being. A light response conduit passes response light from the light director arrangement to a light detector that receives and detects the response light and generates a signal corresponding to the detected light for use in analyzing the live being.

In various applications, the above and other approaches are implemented, for example, in applications such as biological research, the development of new drugs and therapeutics, with the stimulation of a live being, and corresponding detection of a response, facilitated via these approaches.

The above summary is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and approaches, and the invention has been found to be particularly suited for the analysis of live beings, and of live beings in a freely-moving state. While the present invention is not necessarily limited to such applications, various aspects of the invention may be appreciated through a discussion of various examples using this context.

According to an example embodiment of the present invention, an approach to optical analysis with a live being involves the mounting (e.g., coupling or affixing) of a light directing arrangement to the live being in a manner that facilitates the live being's movement while optically analyzing the being. In this context, the being is generally free to move about as would occur under regular living conditions for that being, such as in a home setting (for human beings) or in a controlled environment such as a caged or fenced-in type of setting (e.g., for an animal).

The fixed nature of the light directing arrangement relative to the subject being analyzed facilitates the stimulation of, and corresponding detection of related responses to, target portions in the live being. The light directing arrangement is adapted to direct source light into the being at a selected target location. For instance, in some applications, light is directed to target locations at subcutaneous locations in a live being, such as into brain tissue of a mouse, rat or similar animal. Further, the fixed nature of the light directing arrangement facilitates analysis over time, such as hours, days, weeks or even months; this analysis is thus facilitated while allowing the subject being analyzed to move freely over such time periods under what could be considered otherwise normal life conditions.

The source light is generated in a variety of manners. In some applications, the source light is generated using a light source mounted to the live being; in other applications, the source light is received from an external light source using, e.g., a fiber optic link to present the light to the light directing arrangement. The light is directed into the live being using one or more of a variety of approaches, such as those implementing an actuator, micro-electrical mechanical (MEMS) micro-mirror or other direction approach. In the context of these applications, the source light may be implemented to stimulate a response in the live being, or for collection upon reflection from the live being for approaches such as illumination and/or those involved with the detection of reflective characteristics of the being undergoing analysis.

Light from the being (e.g., reflected or emitted) is directed and/or collected using the light director discussed above and/or another arrangement. Directed light is passed to a detector where the light is detected and used in analyzing the being. The detector is selectively located on the live being (e.g., mounted with the light directing arrangement) or remotely from the live being, with a light conduit type of device used to pass the light to the detector.

In the context of the approaches discussed herein, a variety of live beings may be analyzed using one or more of these approaches. In some applications, the live being is an animal such as a rat, bird or mouse, allowed to generally move freely about a controlled environment such as a cage while undergoing analysis. In certain implementations, the live being is an animal configured (e.g., via genetics, substance injection or viral vector introduction) to generate a particular response, relative to light stimulation. For example, fluorescent markers are selectively injected or genetically engineered into tissue to selectively tag a particular molecular species within specific classes of cells; responses associated with these fluorescent markers are detected and used to analyze the tissue. With these approaches, responses of the live being to particular treatments can be monitored and, where appropriate, monitored over time while facilitating the ability of the live being to move under generally normal conditions. Further, certain response-generating activities such as those related to treatment with pharmaceuticals can be monitored over time, where treatment can be effected to the live being while the being is undergoing analysis.

In various embodiments, the approaches discussed in the previous paragraph are implemented in connection with the analysis of outwardly behavioral aspects of the live being undergoing analysis. For example, responses of a live being to treatment can be monitored using the above approaches while also monitoring behavioral factors of the live being under relatively normal movement conditions. Relative to the analysis of anesthetized beings, these approaches facilitate a real-time analysis of a live being as it experiences relatively normal living conditions. One such approach may involve, for example, the monitoring of brain tissue in a live being over a period of time (e.g., weeks, months or longer) as the live being undergoes a particular treatment; during this time, physical behavior of the live being can also be monitored. Psychological responses and/or characteristics of the live being can be similarly monitored. In this regard, a variety of behaviors such as those relating to drug abuse, athletic performance and learning can be correlated to detected characteristics of underlying cells supporting the behavior over the course of time. Changes in behavior relative to subcutaneous tissue monitoring, at an instant and/or over a period of time, can further be detected and used with corresponding conditions of underlying cells in research and/or treatment of conditions. In some applications, such approaches are used with drug research, facilitating the discovery of new drugs and the testing of new pharmaceutical agents.

Various embodiments are implemented with the observation of both internal response and outward behavior as discussed above. With these approaches, the behavior of cells in physiologic contexts is used to reveal and to confirm native cellular characteristics, where cellular properties mutually interact with organ systems physiology. For example, anesthetized animals may not necessarily experience stress, exercise, fear, hunger, arousal or other conditions that can be implemented with a freely-moving being with approaches discussed herein. In this regard, interplay between cellular mechanisms and physiological factors in alert animals are thus studied using detected responses to stimulation applied via a light directing arrangement as discussed above. Furthermore, certain applications are directed to the examination of cellular underpinnings of phenomena such as problem solving, memory, or social behavior.

In another example embodiment of the present invention, an optical imaging system comprises a light director arrangement and a housing structure. The light director arrangement is adapted to selectively direct stimulation light from a light source to a target area in the live being. The stimulation light generates response light in the target area, and the light director arrangement is adapted to direct the response light from the live being to a light detector. The housing structure is adapted to be fixed to the live being, such as by mounting via screws or glue to tissue, bone or other portions of the live being. The housing structure is further adapted to hold the light director arrangement in relative proximity to the live being to facilitate the selective direction of stimulation light to the target area and to facilitate the direction of the response light. For instance, where the light director arrangement includes a fixed device such as a mirror or fiber optic actuator, the housing is adapted to hold the fixed device in a position that is relative to the live being. In this regard, when the live being moves, the housing holds the fixed device in a consistent position, relative to the position of the target area.

In various example embodiments, an optical imaging system attached to a live being is formed in a relatively compact and lightweight arrangement amenable to use with small beings, such as an adult mouse. For instance, an adult mouse typically used with testing and analysis approaches often can bear up to about 3.5-4 grams of weight on its head while still being able to behave normally. In this regard, light direction and collection components of optical analysis equipment are manufactured in a manner that facilitates equipment exhibiting such light weight, such as by using small-scale devices such as MEMS-type devices (micro-electro-mechanical systems devices). In some applications, the optical imaging system is flexibly implemented so that the live being is free to move around during imaging, with system components that are not mounted directly on the mouse being connected to the mouse by wires, optical fibers, wireless links or other flexible components.

In one example embodiment of the present invention, an optical imaging system employs scanning imaging modality such as two-photon fluorescence imaging, and includes components for scanning a light beam that is delivered to the live being's body. For instance, a laser source can be implemented to direct laser light (e.g., pulsed at a femtosecond rate) via an optic conductor such as a fiber optic cable. The optic conductor is coupled to imaging components at the live being's body. Certain applications are directed to the generation of the laser light at the live being's body, with the light from the laser passed to a target region of the live being directly from the laser or via a relatively short on-body type of light conductor.

In various applications, fluorescence imaging approaches as discussed herein involve multiphoton fluorescence excitation, with multiple photons emitted (e.g., scattered) from a target location in a live being and detected to facilitate three-dimensional imaging. Such approaches facilitate imaging of thin optical sections that can be obtained through hundreds of microns of tissue (e.g., with the point of focus of laser or other light directed to the target location).

Lasers and/or other light sources and arrangements implemented with these approaches are adaptable for directing light to target locations at various portions in a live being. For instance, surface or near-surface structures, such as those at or just below a cutaneous layer, are readily imaged using such approaches. Similarly, deep tissue structures of live beings in a conscious, behaving state can also be imaged, in connection with or independently from near-surface imaging. As discussed at various portions herein, certain deep tissue structures can be imaged using a capillary-type approach, where a semi-permanent capillary is selectively implanted into the live being, leaving an exposed end of the capillary open to acceptance of optical imaging components such as light source (or conduit) and light direction components.

In various implementations, one or more imaging and spectroscopic modalities are used to probe cellular or molecular properties in a freely moving, genetically engineered or transgenic animal such as a mouse, using an attached light direction type arrangement that facilitates optical analysis thereof. Other applications are directed to the analysis of an animal having undergone delivery of viral vectors (e.g., that encode fluorescent or non-fluorescent proteins), or having undergone RNAi (RNA interference). Examples of applicable analysis approaches include, but are not limited to, conventional fluorescence imaging, confocal fluorescence imaging, multi-photon fluorescence imaging, second harmonic generation (SHG), third harmonic generation (THG), Raman spectroscopy, and coherent anti-stokes Raman scattering (CARS), fluorescence lifetime imaging, fluorescence resonance energy transfer (FRET), fluorescence recovery after photobleaching (FRAP), and types of polarization sensitive imaging. Such an imaging system could comprise miniaturized microscopes, endoscopes, or other types of biosensors.

In one particular embodiment, two-photon fluorescence microendoscopy is used to probe cellular and molecular properties in freely moving, genetically engineered mice. Two-photon fluorescence facilitates (e.g., relative to certain confocal modalities for imaging within biological tissue) one or more of: depth sectioning without use of a confocal pinhole, reduced photobleaching and phototoxicity, and reduced scattering through the use of longer wavelength excitation. Moreover, certain applications are directed to the use of a longer wavelength, relative to single-photon fluorescence imaging, to facilitate the nonlinear excitation of a fluorochrome in the being and thereby generally limit the fluorochrome excitation to the point of focus of the photons. Limiting the fluorochrome excitation in this manner facilitates the aforesaid reduced photobleaching and phototoxicity.

In some applications, two-photon fluorescence microendoscope probes are implemented with minimally invasive compound gradient refractive index (GRIN) lenses that are about 350-1000 μm in diameter. The GRIN lens microendoscopes approach is implemented with flexible fiber-optic technology and a stable, compact and lightweight housing for attaching to live beings such as mice. With this approach, the imaging system can be used for probing both surface and deep tissue structures in freely moving beings such as genetically engineered mice. Certain figures and corresponding discussion below describe examples equipment that can be implemented with such applications.

According to another example embodiment of the present invention, an optical imaging system is fastened or coupled to a live being for imaging the live being by selectively implementing one or more approaches as described above. The system includes a light source, light detector, a light director arrangement, a housing, a light conduit that passes source light from the light source to the light director arrangement, and another (common or separate) light conduit that passes response light from the light director arrangement to the light detector.

The light director arrangement is adapted to couple to the live being via the housing and to selectively direct stimulation light from the light source to a target portion in the live being and to direct response light from the live being to the light detector. The housing is fixed to the live being and holds the light director arrangement in a position relative to the live being while the light director arrangement selectively directs stimulation and response light.

The light detector is adapted to receive the light directed from the live being, via the light conduit that passes response light. The light conduits (separably or in combination) may include, for example, one or more of a fiber optic cable, a mirror and an air medium. Furthermore, the light director arrangement may include and/or make up part of one or both of the light conduits.

The light director arrangement is implemented using one or more of a variety of components and approaches, depending upon the application. In one implementation, the light director arrangement includes a fiber optic cable coupled to an actuator, with the actuator adapted to move the fiber optic cable to selectively direct light into the live being (e.g., to scan light across tissue in the live being). In another implementation, the light director arrangement includes a mirror arrangement adapted to move to selectively direct light into the live being, such as via translation and/or rotation.

The light source includes one or more of a variety of types and arrangements of light sources, such as those discussed herein. In one instance, the light source is an external source such as a laser, with light from the source being coupled to the light director arrangement using a fiber optic cable or other means for passing source light. In another instance, the light source is a local source coupled to the light director arrangement and includes, for example, a laser mounted to the housing. Where the laser is local, the light conduit is selectively integrated with the light director arrangement, for example where a MEMS mirror is implemented to receive light from a local laser source and scan that light into the live being.

The light detector arrangement includes one or more of a variety of detectors, such as those discussed herein. The light detector may be located remote to the light director arrangement, with light coupled to the remote detector via a fiber optic cable, a mirror or other device for passing response light. In some instances, a light detector is implemented locally with the light director arrangement and includes, for example, a light responsive component and a communications arrangement for communicating a signal representing the detected light for use in analyzing the live being.

Figure 1:
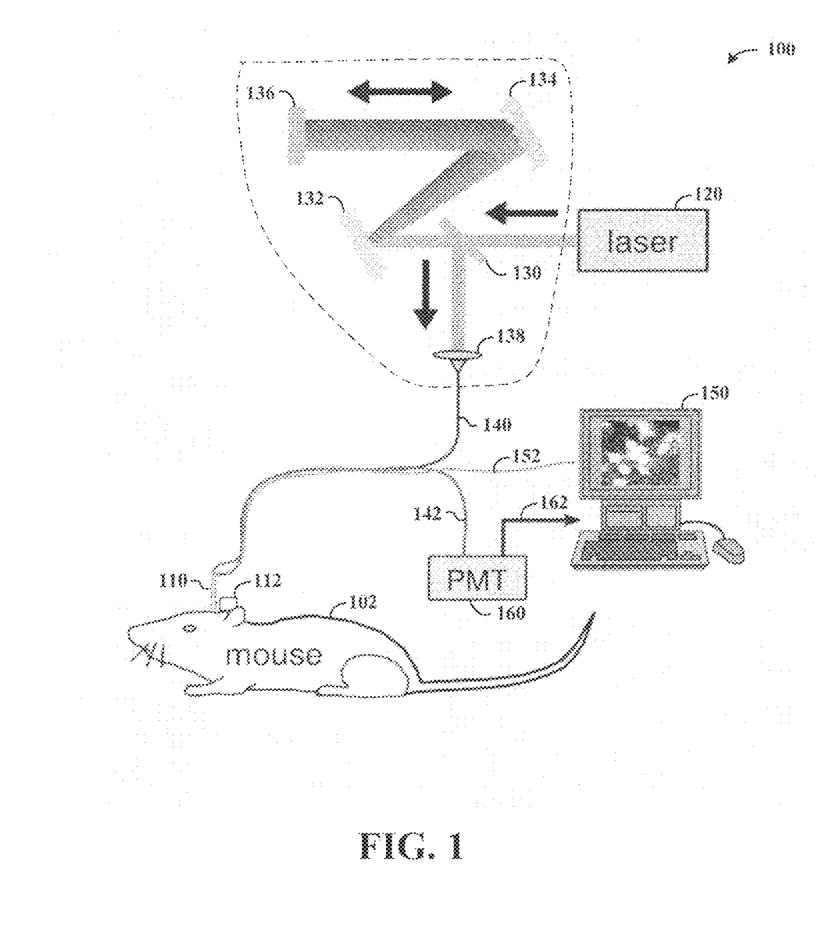
FIG. 1 illustrates an optical analysis system for imaging within a live being, according to an example embodiment of the present invention.

FIG. 1 shows an arrangement 100 that can be implemented with a variety of approaches to two-photon imaging of brain material, such as in a freely moving mouse 102 as shown, according to another example embodiment of the present invention. The arrangement 100 readily facilitates analysis of brain tissue while allowing the being undergoing analysis to move relatively freely (e.g., about a cage), further facilitating the observation of behavioral characteristics of the being. Such an approach is applicable, for example, to those approaches discussed above in connection with the combined analysis of internal and external portions of a being over time to facilitate real-time analysis of responses to drugs or other conditions of treatment. That is, the mouse 102 can be observed for physical or psychological behavior from an outward perspective while correspondingly observing the mouse's brain tissue, with observations being correlated to one another and, where appropriate, to treatment applied to the mouse.

The arrangement 100 includes an endoscope arrangement 110 coupled to a live being (here shown coupled to the mouse 102), and which selectively includes GRIN optics. The endoscope arrangement 110 is implemented using one or more of a variety of devices, such as that shown in and discussed in connection with FIG. 2. In some applications, the endoscope arrangement 110 includes a base 112 adapted to mount to a live being and, in some applications, to actuate, translate or otherwise control endoscope components. For purposes of this discussion, the remaining portions of FIG. 1 are discussed in the context of analyzing the mouse 102; however, as described herein a multitude of different types of live (or non-live) beings are selectively analyzed using a similar approach).

The endoscope arrangement 110 passes light from a light source to the mouse 102, using one or more of a variety of approaches such as scanning, pulsing, or otherwise directing the light. The endoscope arrangement 110 also passes light from the mouse to an external detector. This light from the mouse may include, for example, reflected light and/or emitted light, and in the latter case may include light emitted in response to light directed to the mouse, such as that stimulated via single- or two-photon excitation.

A variety of light sources and accompanying light-directing arrangements can be implemented with the endoscope 110 for analyzing the mouse 102. By way of example, a laser 120 is shown as a light source and may include one or more of a variety of lasers. In some applications, the laser 120 is a Ti:sapphire laser that generates short pulses of laser light at intervals on about a picosecond or femtosecond frequency (e.g., 100-150 fs intervals at 790-810 nm).

Light from the laser 120 is selectively pre-chirped using optics including one or more of a combination of mirrors and gratings or prisms to compensate for possible chromatic dispersion incurred when passing the light to the mouse 102. When such a pre-chirping approach is used, light from the laser 120 is passed via light-directing devices including a (beamsplitting) mirror 130, grating 132 and 134, mirror 136 and lens 138, all of which are selectively included in a common arrangement as suggested by the dashed lines around the same. In this regard, light from the laser 120 is selectively passed through the mirror 130 to the grating 132, on to grating 134 and reflects off of the mirror 136 back through the grating 134 and 132, respectively, and from mirror 130 to lens 138.

The laser light is focused into a light conduit 140, which can be implemented using a variety of light-conducting devices. In this instance, the light conduit 140 is shown by way of example as implemented with a hollow-core photonic crystal fiber that generally mitigates unwanted nonlinear optical effects, such as self-phase modulation, via mode propagation mainly in the air core. When implemented, for example, with a Ti:sapphire laser with short pulses as discussed above, the laser light passes in the lowest-order mode of the light hollow-core photonic crystal fiber.

The light exits the light conduit 140 and enters the endoscope device 110, which focuses the light into the brain of the mouse 102 for exciting tissue therein. The endoscope device 110 is selectively controlled by a computer 150, via a wired link 152 or wireless link for passing control signals (e.g., for scanning or otherwise directing light to the mouse 102). In some applications, the light facilitates two-photon endoscopy via two-photon excitation of tissue in the mouse 102 (or other subject). Fluorescence photons emitted in response to the laser excitation are collected by the endoscope 110 and then delivered using another light conduit 142, shown by way of example as a large-core multimode fiber, to a light detector 160, such as a photomultiplier tube.

The light detector 160 generates an output signal 162 that is passed to the computer 150, which is programmed with image data processing code. The computer 150 uses the output signal 162 to construct an image or other information characterizing the tissue in the mouse 102, and selectively displays the image or information on a monitor. This output is selectively used, as discussed above, to correlate conditions of the tissue in the mouse 102 with behavior of the mouse that is outwardly observable (e.g., by a caretaker, either directly or as monitored electronically).

Figure 2:
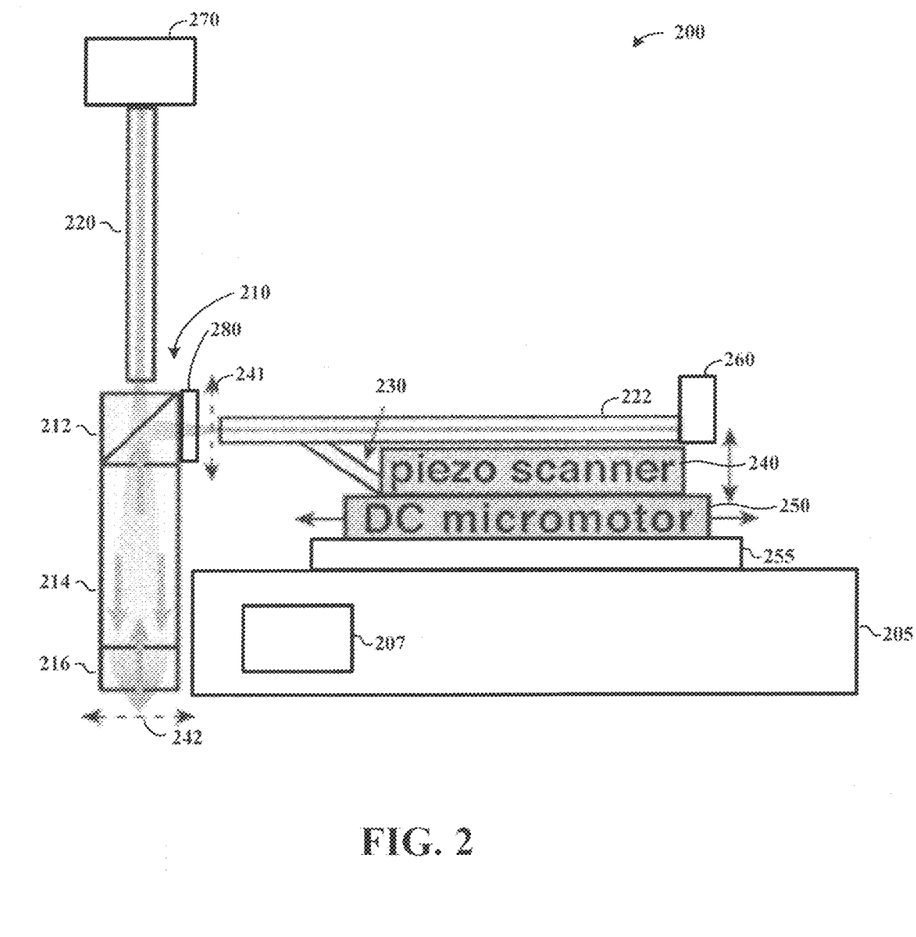
FIG. 2 illustrates optical and electronic components of an imaging device, according to another example embodiment of the present invention.

FIG. 2 shows a microendoscope arrangement 200 adapted for mounting to a live being, according to another example embodiment of the present invention. In some applications, the microendoscope arrangement 200 is implemented with an approach such as that shown in FIG. 1, in connection with the endoscope arrangement 110. A base 205 is used to couple the arrangement 200 to a live being, such as by inserting a fastener such as a screw through the base 205 and into the skull of a mouse for neural observation.

The microendoscope arrangement 200 includes an optics arrangement 210 having a micro-prism 212 (e.g., beam splitter) and a probe arrangement (e.g., a doublet GRIN lens probe) including a relay lens 214 and an objective lens 216 (e.g., implemented with one or more lenses, or a lens array, of glass, plastic or other material). In one application, the objective lens 216 has a 0.48 NA and 0.22 pitch, and the relay lens 214 has a 0.2 NA and 0.14 pitch or a 0.11 NA and 0.18 pitch.

Light received via the coated microprism 212 is passed through the relay lens 214 and the objective lens 216 to a target location of a live being. Light from the live being is passed through the objective lens 216, the relay lens 214 and the micro-prism 212 to a light conduit 220 such as a multimode fiber (e.g., similar to light conduit 142 in FIG. 1, such as a polymer fiber having a 980 micrometer-diameter core and 0.51 NA).

A micromotor 250 and piezo scanner 240 are coupled to a source light conduit 222, such as a photonic bandgap fiber, that supplies light from a source such as a laser. The light conduit 222 may, for example, be implemented in a manner similar to the light conduit 140 in FIG. 1. A stiffening piece 230 is optionally implemented to stiffen or otherwise facilitate a connection between the light conduit 222 and the piezo scanner 240.

The micromotor 250 is optionally coupled to the base 205 via a translation arrangement 255, such as a track, gear or other device that allows controlled movement of the micrometer relative to the base in a manner that moves the light conduit 222 laterally to focus light to the micro-prism 212. In certain applications, the micromotor 250 is fixed and includes a screw, track or gear coupled to the piezo scanner 240 for moving the scanner laterally. For example, the piezo scanner 240 can be clamped to a shuttle that runs along a threaded output shaft of the micromotor 250. An electrical signal applied to the micromotor 250 translates the piezo scanner 240 and light conduit 222 axially with respect to the micro-prism 212. This motion adjusts the location of the light focus (e.g., excitation laser light) within the subject by tens to hundreds of microns and gives the user fine control over the focus.

The piezo scanner 240 (e.g., about 5-10 mm long) is coupled to the micromotor 250 and moves therewith, and is further coupled to the light conduit 222 directly and, in some applications, the stiffening piece 230. In this regard, when the micromotor 250 moves laterally, the piezo scanner 240 and correspondingly, the light conduit 222, move with it. The piezo scanner 240 moves the light conduit 222 in a vertical direction as shown by the double arrow 241, to effect the scanning of the resultant light source as shown by the double-arrow 242. The piezo scanner 240 bends from microns to hundreds of microns in response to an applied voltage, thus actuating the light conduit 222 to scan a target area. A length of the light conduit 222 (e.g., less than one millimeter to tens of millimeters) extends from the piezo scanner 240. The stiffening piece 230 couples the orthogonal axes of the piezo scanner 240, and thus the one-dimensional motion of the piezo scanner causes the tip of the light conduit 222 to move.

Movement of the light conduit 222 is effected in different ways to achieve resultant scanning of a live being. For example, the piezo scanner 240 is selectively actuated to facilitate resonant vibration of the tip of the light conduit 222. In some applications, the stiffening piece 230 or another piece of fiber is implemented between the piezo scanner 240 and the light conduit 222 to facilitate a split in resonant frequencies of lateral vibration. The piezo scanner is correspondingly driven with a voltage signal including both resonant frequencies to drive the tip of the light conduit in a Lissajous pattern, with the ratio of the driving frequencies selected to set the sampling density. In some applications, the Lissajous pattern is demagnified 3.2 to 5.2× (times) at the sample (live being) and is selectively adjusted in size by setting the amplitude of the aforesaid drive voltages. With these approaches, scan fields of up to about 145 to 215 micrometers are selectively achieved, depending on the endoscope probe used. For general information regarding Lissajous patterns and for specific information regarding Lissajous-type patterns that may be implemented in connection with example embodiments discussed herein, reference may be made to F. Helmchen, M. S. Fee, D. W. Tank, and W. Denk, Neuron 31, 903 (2001), which is fully incorporated herein by reference.

In some applications, the translation arrangement 255 provides a third degree of movement in a direction generally perpendicular to the shown movement with double arrows 241 and 242 (i.e., in a Cartesian "Z" direction, where lateral movement of the micromotor 250 is in the "X" direction and the vertical movement with the piezo scanner 240 is in the "Y" direction). With this approach, light from the light conduit 222 can be scanned in a plane.

In one implementation, the arrangement 200 is used to facilitate two-photon excitation fluorescence with a live being, wherein the light conduit 222 is scanned vertically to facilitate the lateral scanning across a sample to which the arrangement 200 is coupled. The piezo actuator scans the light conduit 222 in a two-dimensional Lissajous pattern.

In various applications, the tip of the optics arrangement 210 at the objective lens 216 is placed above or inserted into tissue of a live being and positioned over a target region to be imaged. Light from the live being is passed via the light conduit 220 to a remotely placed optical detector. In some applications, the light conduit 220 is removed and a microscope objective is positioned over the micro-prism 212 to facilitate one-photon fluorescence imaging in an epi-fluorescence configuration.

In one embodiment, the working distance of the system microendoscope arrangement 200 (the distance from the exit face of the relay lens 214 to the focal plane) is selectively set via the optical properties of the particular relay lens chosen and by the distance between the light conduit 222 and the micro-prism 212. This working distance is selected to effect a change in the working distance of the imaging system, and is facilitated further via the adjustment of focus achieved with lateral movement effected via the micromotor 250 as discussed above.

In some applications, a set screw and spring loaded, movable wedge included with the base 205 facilitates the adjustment of the height of the light source optics (micromotor 250, piezo scanner 240 and light conduit 222) with respect to the base. This adjustment may, for example, involve a vertical adjustment of a few millimeters to a few centimeters, and is selectively used for choosing a depth and region within the tissue for imaging. In certain implementations, such a screw and movable wedge are implemented to facilitate the use of different length relay lenses (214) with different optical properties for tailoring the microendoscope arrangement 200 for resolution, field of view and/or working distance conditions in delivering light to a live being. Once the region to be imaged is located, the optics arrangement 210 is left in place, and all subsequent focal adjustments are performed by the micromotor.

In another embodiment, a clip or other fastener holds the piezo scanner 240 and is adapted to swivel about two orthogonal axes, facilitating the alignment of the light conduit 222 to direct light (e.g., excitation laser light) to the center of the micro-prism 212. In some applications, this approach is implemented to compensate for any misalignment of the light conduit 222.

As discussed above, the components described with FIG. 2 can be attached to a compact, protective housing (i.e., base 205) that is mounted to one or more of a variety of live beings, such as a mouse's skull. The weight of the entire device, including the housing and all of the optical and electronic components, is selected to facilitate implementation with the particular live being undergoing imaging. For instance, where a mouse's brain is imaged, the weight is small enough to allow the mouse to carry the device freely on its head (e.g., less than about 4 g for most adult mice) and go about relatively normal activity. The connections between the device mounted on the live being and remotely located components may include, for example, flexible optical fibers for delivering the excitation light and for collecting a response such as light emitted via fluorescence, and any control wires for controlling the piezo scanner 240 and micromotor 250.

In some applications, the endoscope arrangement 200 is controlled via wireless communications to control, for example, the micromotor 250 and piezo scanner 240. A wireless receiver is included with one or both of the micromotor 250 and piezo scanner 240, or otherwise with the arrangement 200 and coupled to control the micromotor and piezo scanner. By way of example, a wireless receiver 207 is shown implemented with the base 205 and communicates using, for example, wireless Ethernet signals, Bluetooth signals, infrared signals or other signals. Control signals received via the wireless receiver are processed and used in the actuation of one or both of the micromotor 250 and piezo scanner 240.

In another example embodiment and referring again to FIG. 2, a light source 260 is implemented at the endoscope arrangement 200 and at the live being. This light source 260 may include, for example, a chip-mounted laser or other small-scale light source. The light conduit 222 is arranged to receive light from the light source 260 and to pass light to the micro-prism 212 as discussed above. In some applications, the light source 260 is mounted to move with the light conduit 222 in response to movement from one or both of the micromotor 250 and piezo scanner 240.

Another example embodiment is directed to the use of a light collector or detector at the endoscope arrangement 200. By way of example, a light detector 270 is shown arranged to receive light via the light conduit 220. The light collector 270 may include, for example, a photomultiplier tube as discussed in connection with FIG. 1 (item 160), or another arrangement adapted to detect light and to generate a signal characterizing detected light. Any such signal generated is passed to an external device, either via a wired connection or via a wireless connection as discussed above (e.g., selectively using wireless receiver 207 or another wireless receiver, separate and/or in connection with the light detector 270.

In another implementation, a tunable lens is implemented in the optical path within the microendoscope device 200 to provide fine focal control. In some applications, the tunable lens is implemented in lieu of the micromotor 250. By way of example, a tunable lens 280 is shown arranged between an end of the light conduit 222 and before the micro-prism 212. In various applications, the tunable lens 280 includes one or more of a liquid lens or a liquid crystal lens (see, e.g., FIG. 3 and discussion below for an example liquid lens that can be implemented in connection with the tunable lens 280). An electrical signal applied to the tunable lens 280 changes the focal length of the lens and thus changes the working distance of the device 200. In this way, focal control is obtained without necessarily implementing moving parts, facilitating relatively small size and complexity.

A multitude of optical analysis approaches are selectively implemented in connection with one or both of FIGS. 1 and 2, in addition to or separately from the approaches discussed above such as two-photon fluorescence imaging. The following approaches are thus selectively implemented with the above-discussed approaches: conventional fluorescence imaging, confocal fluorescence imaging, multi-photon fluorescence imaging, second harmonic generation (SHG), third harmonic generation (THG), Raman spectroscopy, coherent anti-stokes Raman scattering (CARS), fluorescence lifetime imaging, fluorescence resonance energy transfer (FRET), fluorescence recovery after photobleaching (FRAP), and types of polarization sensitive imaging. For these embodiments, appropriate filters and optical elements are selectively implemented in connection with or in alternative to those shown in FIGS. 1 and 2, with the optics and arrangements shown in those figures selectively modified to suit each particular application. Furthermore, one or more embodiments discussed herein are implemented in a manner not inconsistent with that described in Benjamin A. Flusberg, Juergen C. Jung, Eric D. Cocker; Erik P. Anderson, and Mark J.

Schnitzer, "In vivo brain imaging using a portable 3.9 gram two-photon fluorescence microendoscope," OPTICS LETTERS/Vol. 30, No. 17/Sep. 1, 2005, which is fully incorporated herein by reference.

Referring again to FIG. 2, a variety of other approaches to directing light from the light conduit 222 are implemented in various example embodiments. For example, different configurations of piezo actuators could be used with or in an alternative to the piezo scanner 240. In another example, the light conduit 222 is fixed and small-scale mirrors such as MEMS mirrors are used to deflect light from the light conduit 222. A general MEMS mirror approach that may be implemented in connection with such an example embodiment is described in U.S. patent application Ser. No. 11/338,592 (U.S. Pat. No. 7,307,774) entitled "Micro-optical Analysis System and Approach Therefor" and filed on Jan. 24, 2006, which is fully incorporated herein by reference. In addition, the light conduit 222 includes a coherent bundle of optical fibers, with scanning implemented at a distal end of the fiber bundle (i.e., at an end of the light conduit 222 that is opposite the micro-prism 212).

In another example embodiment, a coating on the micro-prism 212 separates source (excitation) and response (fluorescence) light. That excitation light is transmitted through the coated micro-prism while the fluorescence light is reflected off the hypotenuse face thereof.

The micro-prism 212 is replaced with a dichroic mirror in another example embodiment. The dichroic mirror is used to separate source light from the light conduit 222, and response light from the live being undergoing analysis. For example, when the source light passed via the light conduit 222 is laser excitation light used to stimulate a fluorescence response in a live being, the dichroic mirror separates the laser light from fluorescence photons.

Figure 3:
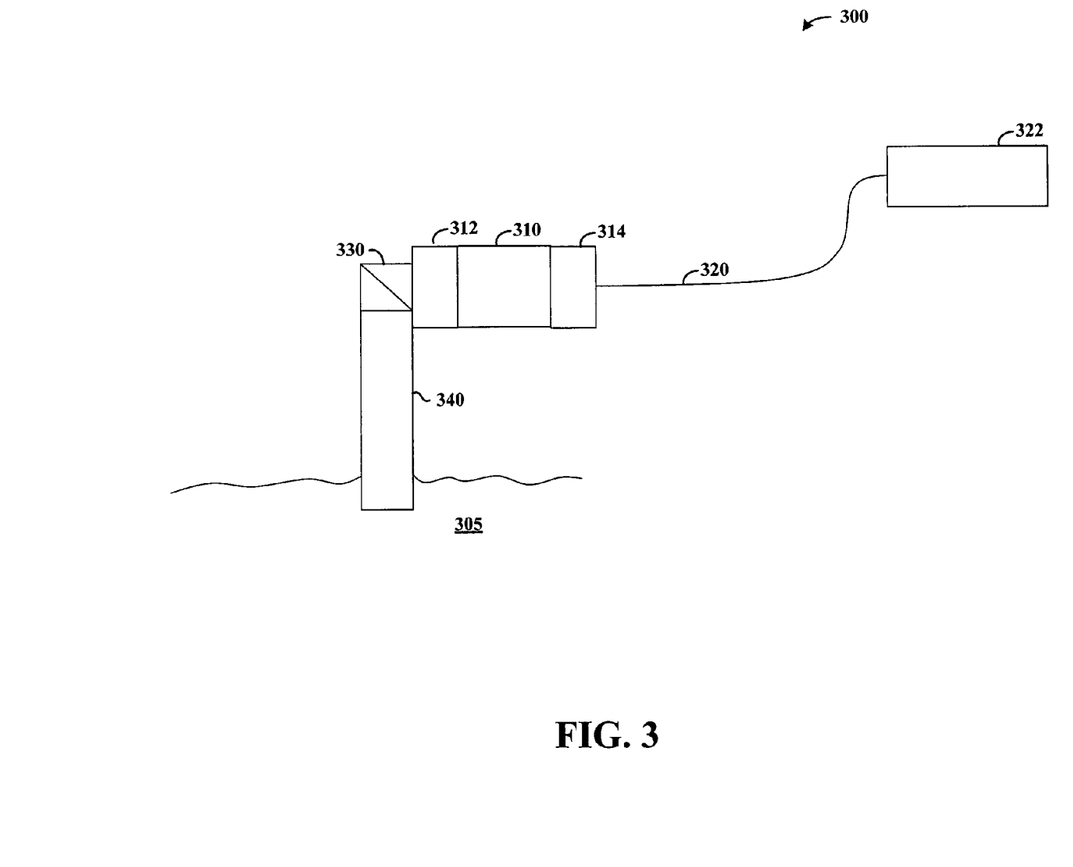
FIG. 3 illustrates a microendoscopy device that includes a liquid lens, according to another example embodiment of the present invention.

FIG. 3 shows a liquid lens arrangement 300 having a liquid lens 310 placed in an optical path between an excitation photonic bandgap fiber 320 and a GRIN endoscope/prism cube 330, according to another example embodiment of the present invention. Excitation light from a laser light source 322 is passed by the photonic bandgap fiber 320 to the liquid lens 310, which passes the light to the GRIN endoscope/prism cube 330 and into a microendoscope probe 340, which directs the excitation laser light to tissue under investigation 305. The approach shown in FIG. 3 may be implemented, for example, in connection with the approaches discussed above with and shown in FIGS. 1 and 2, such as with the tunable lens 280.

A variable voltage is selectively applied to the liquid lens 310 to change the shape of a liquid meniscus inside the liquid lens, and thus changing the liquid lens' focal length. This change in the liquid lens' focal length in turn changes the working distance of the liquid lens arrangement 300.

In some applications, an AC voltage is applied to the liquid lens 310 at a specified frequency to facilitate axial scanning of the tissue 305 for volumetric imaging approaches. In various implementations, other optical elements (e.g., lenses, filters) are placed in the optical path, either before or after the liquid lens 310, with optical elements 312 and 314 shown by way of example.

Figure 4A:
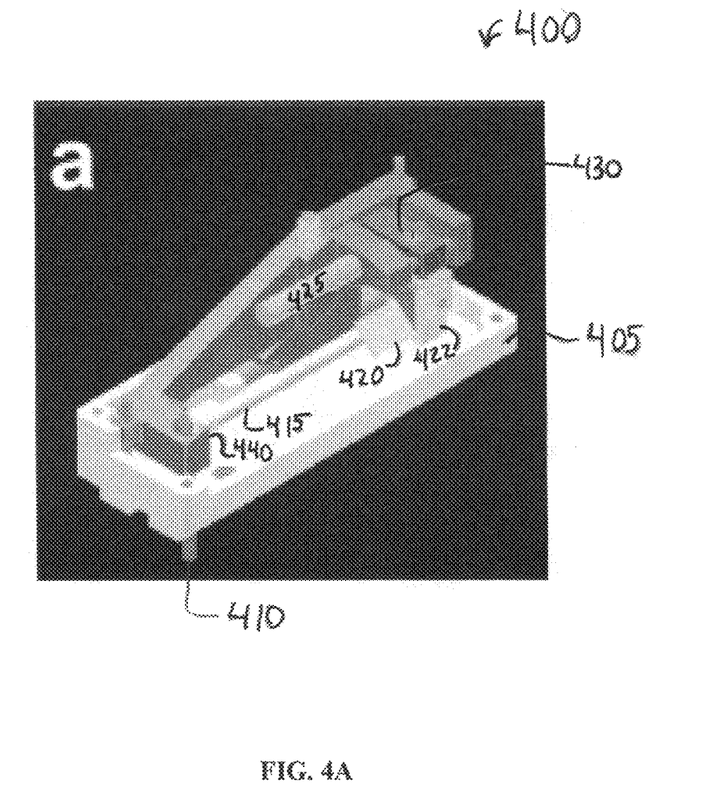
FIGS. 4A and 4B show a microendoscope device, according to other example embodiments of the present invention.
Figure 4B:
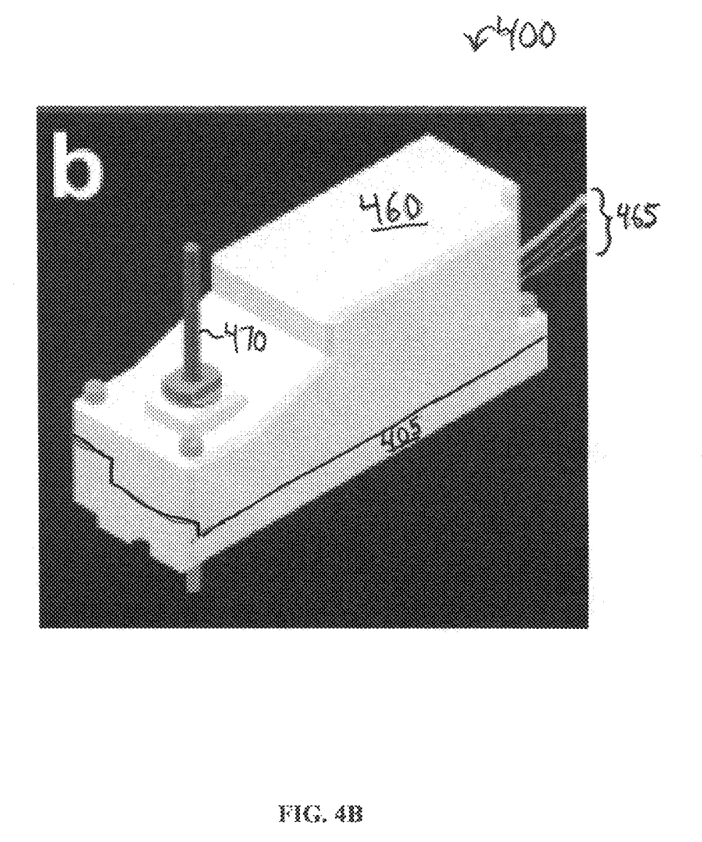

FIGS. 4A and 4B show a microendoscope device 400, according to another example embodiment of the present invention. FIG. 4A shows the device 400 without a cover and FIG. 4B shows the device with a cover in place. These approaches may be implemented, for example, in connection with the example embodiments shown in and described with FIG. 2.

FIG. 4A shows a base plate 405 for mounting a scanning device on a live being's head, such as a mouse's head. A microendoscope probe 410 is arranged to supply excitation light to the live being, the excitation light being supplied via a bandgap optical fiber 415. A piezoelectric actuator 420 held with a piezo clip 422, and micromotor 425 with a shuttle 430, are mounted together on an optical alignment arm. The bandgap optical fiber 415 is glued to the piezoelectric actuator 420 and the fiber is aligned with a micro-prism 440 and the microendoscope probe 410. The arrangement shown in FIG. 4A may, for example, be implemented in a manner similar to that shown in and discussed in connection with FIG. 2, with similar items implemented in a similar manner as appropriate.

In FIG. 4B, a protective housing 460 is shown coupled to the base plate 405. Optical and electrical inputs 465 respectively pass excitation light into the microendoscope device 400 and pass electrical signals into (and, where appropriate, from) the microendoscope device. A light conduit 470 passes light detected from the live being to an external analysis arrangement such as a light detector. The housing 460 and/or base plate 405 and/or various components shown therewith include materials such as Delrin, nylon, titanium, and stainless steel. In one implementation, the dimensions of the housing are approximately 35×15×8 mm, with the microendoscope device 400 weighing less than about 4 grams. The protective housing 460 is further selectively removed and/or modified to facilitate epifluorescence imaging using a microscope objective; this approach is used, for example, to determine whether fluorescent objects are in the field of view prior to laser-scanning imaging as discussed above.

Figure 5:
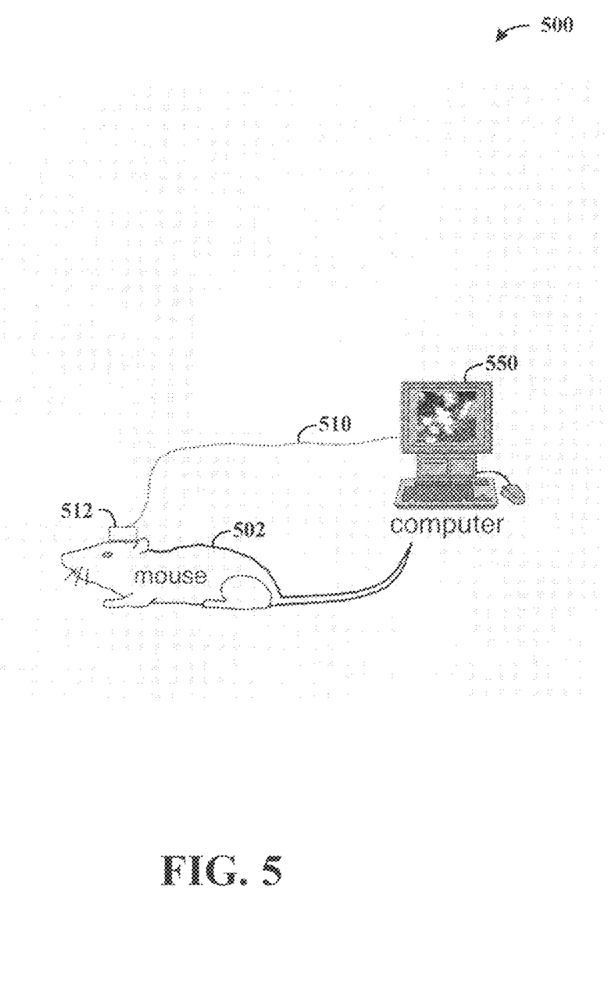
FIG. 5 illustrates an optical analysis device in which a laser source and light detector are embedded in a chip that is mountable on the head of a live being, according to another example embodiment of the present invention.

FIG. 5 shows an arrangement 500 for scanning light to tissue in a freely-moving, live being 502, according to another example embodiment of the present invention. The approach shown in FIG. 5 may, for example, be implemented using an approach similar to that discussed above in connection with FIG. 1.

A chip 512 includes a laser source and light detector and is mounted on a live being's head, here shown as a mouse by way of example. The laser source passes light into the mouse's brain and the light detector detects light emitted, reflected or otherwise passed via the mouse's brain. Electronic control lines 510 couple the chip 512 to a computer 550 and pass information from the light detector that can be used to characterize the light from the mouse's brain. In some implementations, the electronic control lines are omitted and a wireless signal is passed between the computer and the chip to facilitate communications therebetween.

In some applications, the arrangement 500 includes an optics and/or mechanical arrangement that effects scanning of laser light. For instance, one such application involves the generation of laser light on-chip with the chip 512, and directing the laser light via one or more micromirrors as discussed hereinabove. The one or more micromirrors are controlled to facilitate the scanning.

The various embodiments described above and shown in the figures are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For example, a variety of types of light sources, light conduits, actuators and optics can be implemented in connection with and/or as an alternative to those shown in the figures. These approaches are implemented in connection with various example embodiments of the present invention. Such modifications and changes do not depart from the spirit and scope of the present invention, including that set forth in the following claims

What is claimed is:

1. A method for in vivo analysis of a freely-moving live being, the method comprising;
   a) fixing a housing to the live being, wherein the housing encloses therein a light-directing arrangement, wherein the light-directing arrangement comprises a light source to provide stimulation light, and wherein a combined weight of the housing and the light-directing arrangement comprising the light source is less than 4 grams;
   b) passing stimulation light through the light-directing arrangement;
   c) using the light-directing arrangement, providing the stimulation light to a target portion of the freely-moving live being while the freely-moving live being moves about, wherein said stimulation light induces response light from said target portion;
   d) passing the response light from the target portion to a light detector;
   e) at the light detector, receiving and detecting the response light, and generating a signal corresponding to the detected light; and
   f) generating a cellular resolution image of said target portion using said signal.

2. The method of claim 1, wherein providing the stimulation light to the target portion includes selectively scanning stimulation light across the target portion.

3. The method of claim 1, wherein fixing the housing includes fixing the housing to the live being for a period of days, wherein providing stimulation light includes providing stimulation light at several instances over the period of days and wherein receiving and detecting the response light includes receiving and detecting the response of the live being to the stimulation light provided at the several instances.

4. The method of claim 3, further comprising observing outward behavior of the live being over the period of days and comparing the detected response to the outward behavior.

5. The method of claim 3, further comprising applying a treatment condition to the live being, wherein detecting the response of the live being includes detecting a response of the live being to the treatment condition.

6. The method of claim 1, wherein the live being is one or more of the following: a genetically engineered animal, a transgenic animal, an animal having undergone delivery of viral vectors that encode proteins, or an animal having undergone delivery of RNAi.

7. The method of claim 1, wherein the live being expresses a fluorescent protein and wherein providing the stimulation light to the target portion includes stimulating the fluorescent protein, and wherein receiving and detecting the response light includes detecting fluoresced photons from the fluorescent protein.

8. The method of claim 1, further comprising injecting the live being with a molecule that facilitates a fluorescent response to the provided light, and detecting the fluorescent response.

9. The method of claim 1, wherein providing the stimulation light includes providing pulsed laser light at a wavelength selected to facilitate nonlinear excitation of a fluorochrome in the live being.

10. The method of claim 9, wherein receiving and detecting the response light includes detecting photons as a non-linear response of the target portion.

11. The method of claim 9, wherein providing the pulsed laser light includes providing laser light having a wavelength that limits the fluorochrome excitation to a point of focus of the provided laser light.

12. The method of claim 1, wherein said generating a cellular resolution image comprises fluorescence imaging.

13. The method of claim 12, wherein said fluorescence imaging is selected from one or more of the following: confocal fluorescence imaging, multi-photon fluorescence imaging, fluorescence lifetime imaging, fluorescence resonance energy transfer, or fluorescence recovery after photobleaching.

14. The method of claim 12, wherein said generating a cellular resolution image comprises types of polarization sensitive imaging.

15. The method of claim 1, comprising generating a cellular resolution image while said live being is freely moving about as under regular living conditions.

16. The method of claim 1, wherein the live being is a rat, bird, or mouse.

17. The method of claim 16, wherein the live being is a mouse.

18. The method of claim 17, wherein the housing is fixed onto a head of the mouse.

19. The method of claim 1, wherein said target portion comprises brain tissue.

20. The method of claim 1, wherein said response light is limited to a limited point of focus of said stimulation light to said target portion.

21. The method of claim 1, comprising passing said stimulation light to said target portion while said freely moving live being is moving about said live being's home setting.

22. The method of claim 1, wherein said light-directing arrangement is operably coupled via wireless links to an external device.

23. The method of claim 22, wherein the external device is a computer which is configured to selectively control one or more components of the light directing arrangement.

24. The method of claim 1, wherein said generating said image of said target portion occurs while said freely moving live being is generally free to move about as would under regular living conditions.

25. The method of claim 1, further comprising holding the light-directing arrangement via a coupling in a position relative to the live being.

26. The method of claim 1, wherein the light-directing arrangement comprising the light source and enclosed in the housing further comprises the light detector.

27. The method of claim 1, wherein the light-directing arrangement comprising the light source and enclosed in the housing further comprises a GRIN lens.

28. The method of claim 27, wherein the GRIN lens is about 30-1000 μM in diameter.

29. The method of claim 1, wherein the light-directing arrangement comprising the light source and enclosed in the housing further comprises a MEMS mirror.

30. The method of claim 1, wherein the light-directing arrangement comprising the light source and enclosed in the housing further comprises an objective lens.

31. The method of claim 1, wherein the light-directing arrangement comprising the light source and enclosed in the housing further comprises a dichroic mirror.

32. The method of claim 1, wherein the housing has a dimension of about 35 mm or less.

33. The method of claim 1, wherein the housing comprises a base plate and a protective cover that is selectively removable from the base plate.

* * * * *